(12) United States Patent
Møller et al.

(10) Patent No.: US 8,708,978 B2
(45) Date of Patent: Apr. 29, 2014

(54) ARTICLE TO BE INSERTED IN A BODY CAVITY HAVING BIOLOGICALLY INHIBITING SURFACES AND USE AND PREPARATION OF THE ARTICLE

(75) Inventors: Per Møller, Esrum (DK); Anette Alsted Rasmussen, Kokkedal (DK)

(73) Assignee: Impactcare ApS, Rungsted Kyst (DK)

( * ) Notice: Subject to any disclaimer, the term of this patent is extended or adjusted under 35 U.S.C. 154(b) by 513 days.

(21) Appl. No.: 11/886,449

(22) PCT Filed: Mar. 17, 2006

(86) PCT No.: PCT/DK2006/000154
§ 371 (c)(1),
(2), (4) Date: Sep. 14, 2007

(87) PCT Pub. No.: WO2006/097109
PCT Pub. Date: Sep. 21, 2006

(65) Prior Publication Data
US 2008/0140052 A1 Jun. 12, 2008

Related U.S. Application Data

(60) Provisional application No. 60/662,795, filed on Mar. 18, 2005.

(30) Foreign Application Priority Data

Mar. 17, 2005 (DK) ................................. 2005 00387

(51) Int. Cl.
*A61M 5/32* (2006.01)

(52) U.S. Cl.
USPC .............. 604/265; 205/316; 205/317; 427/58

(58) Field of Classification Search
USPC ......... 604/265, 544, 96.01, 164.01, 523, 264; 424/423; 427/122, 58; 205/316, 317; 128/200.26

See application file for complete search history.

(56) References Cited

U.S. PATENT DOCUMENTS

| 4,569,673 A | 2/1986 | Tesi |
| 5,295,979 A | 3/1994 | DeLaurentis et al. |

(Continued)

FOREIGN PATENT DOCUMENTS

| EP | 0586324 | 3/1994 |
| EP | 0591091 | 4/1994 |

(Continued)

OTHER PUBLICATIONS

Percival, S. L. et al., "Bacterial Resistance to Silver in Wound Care", Journal of Hospital Infections, 2005, vol. 60, No. 1, pp. 1-7.

(Continued)

*Primary Examiner* — Kami A Bosworth
*Assistant Examiner* — Imani Hayman
(74) *Attorney, Agent, or Firm* — Winston & Strawn LLP

(57) ABSTRACT

An article to be inserted in a human or animal body cavity, use of the article and preparation thereof. The article has a biologically inhibiting arrangement of electrically connected electrode materials in direct contact with each other on one or more surfaces of the article. The arrangement includes as electrode materials a metallic anode material and a cathode material, where the potential of the cathode material is higher than the potential of the anode material. The cathode material is an electrically conductive material selected among certain non-metallic materials. The arrangement provided on the article releases biological inhibiting ions of the metallic anode material or complexes of such ions when the biologically inhibiting arrangement is contacted with a body fluid. The article can be designed with a controlled release rate suitable for the purpose in question for example an initial high rate of ion release after insertion of a catheter to combat bacteria introduced during the insertion followed by a prolonged release at a lower rate to maintain a low level of bacteria.

24 Claims, 6 Drawing Sheets

(56) References Cited

U.S. PATENT DOCUMENTS

| | | | |
|---|---|---|---|
| 5,322,520 A | 6/1994 | Milder | |
| 5,520,664 A * | 5/1996 | Bricault et al. | 604/265 |
| 5,681,575 A * | 10/1997 | Burrell et al. | 424/423 |
| 5,695,857 A | 12/1997 | Burrell et al. | |
| 6,267,782 B1 * | 7/2001 | Ogle et al. | 623/1.1 |
| 6,273,875 B1 | 8/2001 | Siman et al. | |
| 6,287,484 B1 | 9/2001 | Hausslein et al. | |
| 6,322,588 B1 | 11/2001 | Ogle et al. | |
| 6,808,738 B2 | 10/2004 | DiTizio et al. | |
| 2004/0049145 A1 * | 3/2004 | Flick | 602/41 |
| 2004/0199086 A1 | 10/2004 | Crisp | |

FOREIGN PATENT DOCUMENTS

| | | |
|---|---|---|
| EP | 1536848 | 6/2005 |
| GB | 2287473 | 9/1995 |
| WO | WO-98/31420 | 7/1998 |
| WO | WO-99/46780 | 9/1999 |
| WO | WO-2004/045577 A | 6/2004 |
| WO | WO-2004/045577 A1 | 6/2004 |

OTHER PUBLICATIONS

Yahya, Moyasar T. et al., "Disinfection of Bacteria in water systems by using Electrolytically Generated Copper: Silver and Reduced Levels of Free Chlorine", Canadian Journal of Microbiology, 1990, vol. 36, No. 2, pp. 109-166.

Kark, R.M. et al., *A Primer of Urinanalysis*, 1964, 2nd ed. New York: Hoeber Medical Division, Harper & Row Publishers.

* cited by examiner

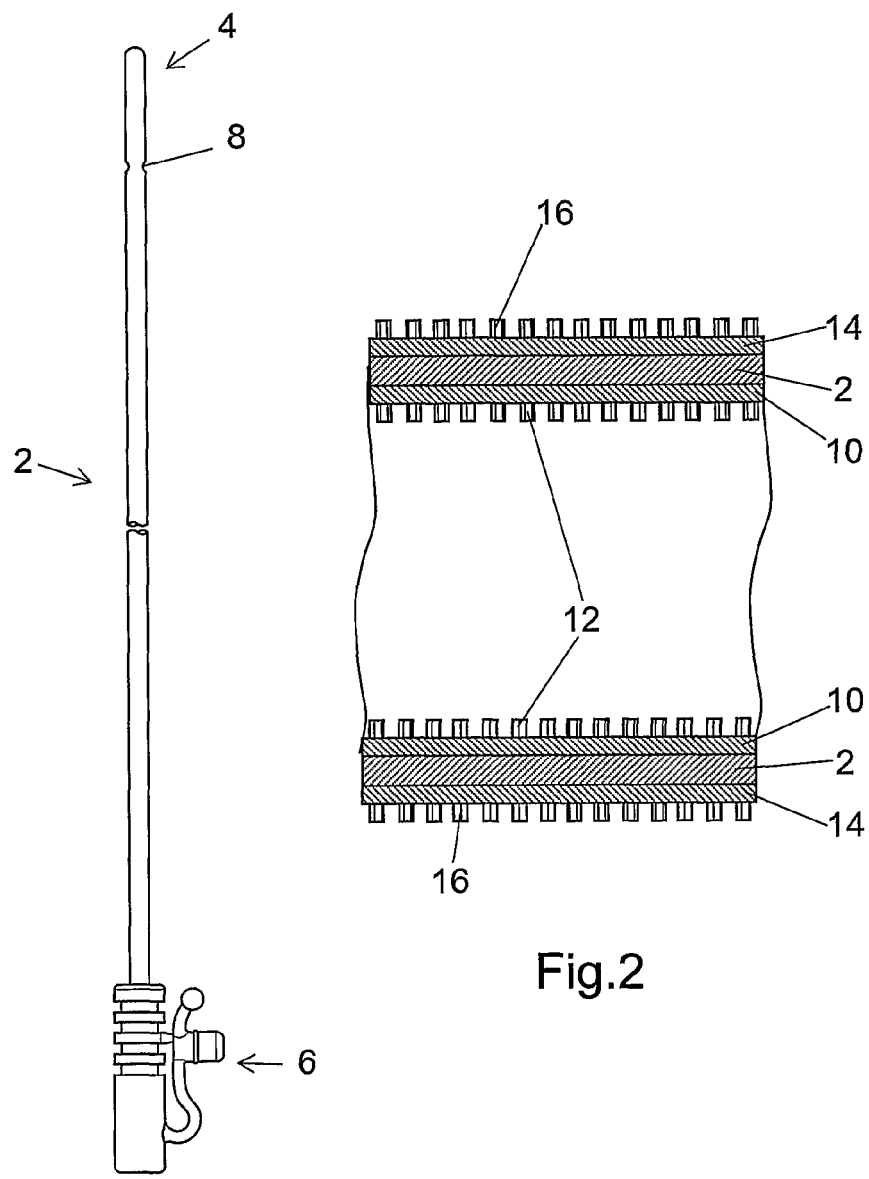

ARTICLE TO BE INSERTED IN A BODY CAVITY HAVING BIOLOGICALLY INHIBITING SURFACES AND USE AND PREPARATION OF THE ARTICLE

TECHNICAL FIELD

The present invention relates to an article to be inserted in a human or animal body cavity having a biologically inhibiting arrangement of electrically connected electrode materials on one or more surfaces of the article, which arrangement as electrode materials includes a metallic anode material and a cathode material, where the potential of the cathode material is higher than the potential of the anode material, which arrangement releases biological inhibiting ions of the metallic anode material or complexes of such ions when the biologically inhibiting arrangement is contacted with a body fluid, the use of an article having a biologically inhibiting arrangement on one or more surfaces for the inhibition of microorganisms and a process for the preparation of an article having a biologically inhibiting arrangement on one or more surfaces.

TECHNICAL BACKGROUND

Articles for temporary insertion in human or animal body cavities, such as catheters and drainage systems, involve a considerable risk of infections. U.S. Pat. No. 5,295,979 (DeLaurentis et al.) states that about 40 percent of patients using urinary catheters develop urinary tract infections in the United States. About 3.2 percent of the total number develop bacteriaemia (bacteria in the blood). In the United States ten to twenty thousand people die each year, and about one billion dollars are expended to manage the complications arising from the use of urinary catheters and drainage systems. Clearly, any means which helps to reduce such infections may have a significant effect on the overall cost of medical services. Furthermore, a lot of pain, suffering, and malaise could be avoided if such infections were combated.

To this end the above U.S. Pat. No. 5,295,979 (DeLaurentis et al.) proposes a urinary catheter with a drain lumen which is coated with oligodynamic metal such as silver and arranged with a coating of a more noble metal such as platinum for creating an iontophoretic galvanic couple, which drives antimicrobial ions into solution. The exterior of the catheter is also coated in a similar manner to inhibit microbes migrating toward the bladder along the outer surface of the catheter.

The use of a noble metal such as platinum for a coating on a catheter or another article to be inserted in a body cavity is per se an expensive solution of the above discussed problem. A large number of such articles to be inserted in the body are disposable articles to be used only once which emphasises the need for a less expensive solution.

It has now been found that an alternative arrangement to the above mentioned arrangement of a metal able to form antimicrobial ions such as silver and a more noble metal such as platinum for creating a galvanic couple, which drives antimicrobial ions into solution can be obtained by the substitution of the noble metal with certain conductive non-metallic materials.

WO 2004/045577 (Møller et al.) discloses a biologically inhibiting material having a surface with separated areas of anode material and cathode material. Both the anode material and the cathode material have a positive galvanic potential, and the potential of the cathode material is higher than the potential of the anode material. The distance between any point on the active surface and the adjacent cathode material and the adjacent anode material does not exceed 200 µm. This material is useable as a construction material in equipments for food preparations or in water systems and is able to inhibit microorganisms by a galvanic process without release of significant amounts of $Ag^+$-ions to a contacting liquid (electrolyte). This special galvanic process is not possible if the contacting liquid contains compounds able form complexes with the $Ag^+$-ions as the case is with body fluids. Thus the biologically inhibiting material disclosed in WO 2004/045577 (Møller et al.) is not intended for use inserted in a human or animal body cavity.

Further to U.S. Pat. No. 5,295,979 (DeLaurentis et al.) examples of articles suitable for insertion in body cavities are also disclosed in U.S. Pat. No. 6,287,484 (Hausslein et al.), GB 2,287,473 (Franks) and WO 98/31420 (Elliott et al.).

WO 99/46780 (Milder et al.) discloses a silver ion releasing material having a plurality of carbon granules and a plurality of silver granules each distributed in an electrically conducting base material. Being distributed separated in the base material the carbon and silver granules are not in direct contact with each other. This arrangement gives not a satisfactory release of the silver ions due to an insufficient electrical contact between the silver anode material and the graphite cathode material.

It has now been found that an alternative arrangement to the above mentioned arrangement disclosed in U.S. Pat. No. 5,295,979 (DeLaurentis et al.) based on a metal able to form antimicrobial ions such as silver and a more noble metal such as platinum for creating a galvanic couple, which drives antimicrobial ions into solution can be obtained by the substitution of the noble metal with certain non-metallic materials.

BRIEF DESCRIPTION OF THE INVENTION

The present invention relates to an article to be inserted in a human or animal body cavity having a biologically inhibiting arrangement of electrically connected electrode materials on one or more surfaces of the article, which arrangement as electrode materials includes a metallic anode material and a cathode material, where the potential of the cathode material is higher than the potential of the anode material, which arrangement releases biological inhibiting ions of the metallic anode material or complexes of such ions when the biologically inhibiting arrangement is contacted with a body fluid, characterised in, that the cathode material is an electrically conductive material selected among nitrides, borides, carbides, mixed nitrides, silicides, oxides with spinel structure, conductive polymers and combinations of two or more thereof and that the cathode and anode materials are in direct contact with each other.

In a preferred embodiment the inventive article to be inserted in a body cavity is as a catheter, a gastroenteral or endotracheal tube, or a part of a drainage or suction device.

The invention also relates to the use of an article having a biologically inhibiting arrangement of electrically connected electrode materials on one or more surfaces of the article, which arrangement as electrode materials includes a metallic anode material and a electrically conductive cathode material, where the potential of the cathode material is higher than the potential of the anode material, which conductive cathode material is selected among nitrides, sulfides, borides, carbides, mixed nitrides, silicides, oxides, carbon, conductive polymers and combinations of two or more thereof, which cathode and anode materials are in direct contact with each other, and which arrangement releases biological inhibiting ions of the metallic anode material or complexes of such ions when the biologically inhibiting arrangement is contacted with a body fluid for the inhibition of microorganisms.

Furthermore, the invention relates to a process for the preparation of an article having a biologically inhibiting arrangement on one or more surfaces of the article which by contact with a body fluid releases biological inhibiting ions of a metallic anode material or complexes of such ions, characterised by providing an arrangement of electrically connected electrode materials on one or more surfaces of the article, which arrangement as electrode materials includes a metallic anode material and a electrically conductive cathode material, where the potential of the cathode material is higher than the potential of the anode material, which conductive cathode material is selected among nitrides, sulfides, borides, carbides, mixed nitrides, silicider, oxides, carbon, conductive polymers and combinations of two or more thereof, and which cathode and anode materials are arranged in direct contact with each other.

The proposed use of nitrides, sulfides, borides, carbides, mixed nitrides, silicider, oxides, carbon, conductive polymers or combinations of two or more thereof as an alternative to the expensive noble metal such as platinum as proposed by DeLaurentis et al in U.S. Pat. No. 5,295,979 opens the possibility for the production of non-expensive disposable articles having biologically inhibiting surface arrangements. Furthermore, some of the proposed cathode materials are more easy to deposit as a layer on certain problematic substrates such as polymeric substrates and it can be more easy to cover such layer with an incomplete layer of a metallic anode material such as Zn, Ag or Cu.

The extent of applicability of the invention appears from the following detailed description. It should, however, be understood that the detailed description and the specific examples are merely included to illustrate the preferred embodiments, and that various alterations and modifications within the scope of protection will be obvious to persons skilled in the art on the basis of the detailed description.

DETAILED DESCRIPTION OF THE INVENTION

The electrically conductive material to be used as the cathode material in the biologically inhibiting arrangement on one or more surfaces of the inventive article can in principle be any electrically conductive material having a potential which is higher than the potential of the metallic anode material in the environment of a human or animal body cavity. Excluded from the present invention are the expensive noble metals disclosed by DeLaurentis et al in U.S. Pat. No. 5,295,979.

Examples of suitable cathode materials having a higher potential than for example silver can be found among
nitrides, especially nitrides of Fe, Ga, Cr, Ti, such as chromium nitride (CrN), titanium nitride (TiN) and titanium aluminium nitride (TiAlN) as well as carbonitrides such as titanium carbonitride (TiCN);
borides, especially borides of Mg, Ti, Nb, Mo, Zr, Cr, Ca, Ta, W and Fe such as titanium diboride ($TiB_2$); niobium diboride ($NbB_2$), molybdenum boride (MoB), zirconium diboride ($ZrB_2$), chromium diboride ($CrB_2$), calcium boride ($CaB_6$), tantalum diboride ($TaB_2$) and tungsten boride (WB);
carbides, especially carbides of Si, Mo, Nb, Ta, Ti, Fe, V, B and W, such as silicon carbide (SiC), molybdenum carbide ($Mo_2C$), niobium carbide (NbC), tantalum carbide (TaC), titanium carbide (TiC) and tungsten carbide (WC);
conductive oxides with spinel structure such as magnetite ($Fe_3O_4$) and chromite ($FeCr_2O_4$) and other conductive compounds of the general formula:

$$XY_2O_4$$

where X is a divalent cation, such as Mg, Zn, Fe, and Mn, and Y is a trivalent cation, such as Al, Fe, Mn and Cr; and
conductive polymers, such as polyaniline, polypyrrole, polythiophene, polyacetylene, polythiophene, poly[3,4-dialkoxythiophene], poly[3,4-ethylenedioxythiophene] and poly[3,4-ethylenedioxythiophene]poly-(styrenesulfonate) and other conductive polymers known in the art.

Suitable as the cathode material are also combinations of two or more of these materials.

Specially preferred as the cathode material are TiAlN, TiCN, SiC, CrN, $TiB_2$, $Fe_3O_4$, TiN, $Cr_2N$, TiC, and $Fe_3C$ including combinations of two or more thereof.

The actual potential difference between the anode and the cathode depends on the selected cathode material, the selected anode material, the area and geometric shape of the electrodes and the composition of the electrolyte in question. The release rate of the biological inhibiting ions of the metallic anode material or complexes of such ions depends inter alia on this actual potential difference and the kinetic properties of the cathode material. When a certain anode material having an appropriate potential, kinetically properties and area has been selected the release rate may be adjusted or controlled by a proper selection of a cathode material having an appropriate potential. To obtain a suitable potential one of the above mentioned cathode materials or a combination of two or more thereof can be selected. Thus a broad range of desirable release rates are available on the basis of the selected cathode material or materials as well as the selected geometric design of the electrodes.

A further possibility for the adjustment of the release rate of the biological inhibiting ions can be obtained by improving the conductivity of the cathode material by doping thereof.

In fact it is also possible to make certain non-conductive or sparingly conductive materials electrically conductive by doping. Such doping extends the selection of possible cathode materials for the inventive article. As a non limiting example several ceramics which are marketed with a content of contaminants improving their electrical conductivity are contemplated for use as cathode materials in the inventive article.

As appears from the above a great variety of non-metallic materials can be contemplated as the cathode material used in the inventive articles. Based on the present specification the skilled person is taught how to select and test a candidate material based on the price, the workability and the electrical conductivity of the material and its potential in the environment of the body cavity in question. Thus, although the materials disclosed in the present description and claims at present are considered as the preferred materials other materials and compositions are also contemplated as the cathode materials.

An important feature of the present invention is the possibility to select among a great number of materials whereby the desired release rate of biological inhibiting ions to a great extent can be tailored. Preliminary tests have shown that granules of graphite deposited with Ag provide a relatively fast release rate of ions. This may be advantageous in articles to be inserted for a short time in a body cavity especially if the risk of infection is high. On the other hand it is often desirable to provide a long lasting slower release rate in case of for example a catheter which is kept in a body cavity for a longer period of time. To this end cathode materials having a potential with a smaller difference to that of the anode material are preferred.

It is also possible to design an article with a controlled pattern of release rates over time using different anode/cathode combinations. As an example a first anode/cathode combination may be selected to obtain an initial high release rate to kill bacteria introduced during insertion of a catheter combined with a second anode/cathode combination with a slow release rate ensuring a long-term bactericidal effect.

In a preferred embodiment of the inventive article the arrangements in two or more areas on the surface of the article may be provided with different release rates of biological inhibiting ions. In this way the article may be tailored to meet the varying requirements for inhibition of microorganisms on the different surface areas of the article when inserted in a body cavity.

It should be noted that the relevant potential of an electrode material, such as for example the potential of the metallic anode material, is the actual potential when being in contact with a body fluid. Thus, as an example, in case the body fluid is a urine containing fluid the potential of silver will decrease relative to the standard hydrogen electrode (SHE) because the dissolved silver ions in the electrolyte are complex bound due to the formation of a complex with the ammonium ions in the urine.

Useful examples of the metallic anode material are Zn, Ag and Cu. The preferred anode material is Ag. It is also possible to use a combination of Zn, Ag and/or Cu either as alloys or distributed as a plurality of individual anode sections each connected electrically to the cathode material. A biological inhibiting arrangement based on such combinations will release a combination of biological inhibiting ions of each type of the metallic anode materials or complexes of such ions when the biologically inhibiting arrangement is contacted with a body fluid. Such release of different metal ions, for example of Ag and Cu, is believed to have a synergistic biological inhibiting activity (Yahya, M. T., Landeen, L. K., Messina, M. C., Kutz, S. M., Schulze, R., & Gerba, C. P. (1990). Disinfection of bacteria in water systems by using electrolytically generated copper:silver and reduced levels of free chlorine. Canadian Journal of Microbiology, 36, 109-116.)

The antimicrobial effect of ionic silver against a broad range of microorganisms is well known and as a consequence is silver included in many commercially available healthcare products. In S. L. Percical, P. G. Bowler D. Russell. Bacterial resistance to silver in wound care. Journal of hospital Infections, Vol. 60, 2005. the risk of development of bacterial resistance is discussed and concluded to be relatively low. According to the present invention it is notable that such risk can be minimized by use of one of the above mentioned combinations of silver with Cu and/or Zn as the anode material.

The biological inhibiting arrangement on the inventive article includes the anode and cathode materials in an arrangement creating a galvanic couple, which drives antimicrobial ions or complexes thereof into a body fluid contacting the arrangement. In the preferred embodiment the arrangement creates multiple small galvanic couples distributed throughout the arrangement. In a useful embodiment such arrangements are provided on those surfaces of an article susceptible to contamination with microorganisms.

According to an embodiment such multiple galvanic couples may be obtained with an arrangement wherein at least one of the electrode materials is distributed as a plurality of sections each in direct contact with the other electrode material. In this way the sections of the relevant electrode material will be active as small electrodes when contacted with a body fluid. Typical sizes of such electrodes may be in the range from 1 nm up to 10 µm or more.

According to a further embodiment such multiple galvanic couples may be obtained with an arrangement wherein a layer of one of the electrode materials is covered with an incomplete layer of the other electrode material.

According to yet a further embodiment such multiple galvanic couples may be obtained with an arrangement wherein particles or flakes of one of the electrode materials contaminated with the other electrode material are immobilized, for example on a non-conductive polymeric matrix.

In a useful embodiment such particles may be incorporated in a matrix used as a coating on an article to be inserted in a body cavity such as a catheter, a gastroenteral or endotracheal tube, or a part of a drainage or suction device. As an example the coating may be of the type having friction-reducing properties in wet condition conventionally used on catheters. Examples of such coatings are disclosed in EP 586 324 and EP 591 091.

According to a still further embodiment such multiple galvanic couples may be obtained with an arrangement comprising a pattern of electrically connected and directly contacting layers of the anode material and the cathode material applied on separated surface areas.

An example of the inventive article is a catheter tube provided with a biologically inhibiting arrangement such as a coating on the interior and exterior surfaces.

According to a preferred embodiment the anode material and/or the cathode material have been applied on the article by a plating method, preferably by electroless plating, electrochemical plating, physical vapour deposition process (PVD-process), chemical vapour deposition process (CVD-process), thermal spraying or a combination of two or more of these processes.

In a further preferable embodiment the anode material and/or the cathode material have been applied on one or more surfaces of the article as a powder. For example is it possible to apply the powder by a painting or printing method incorporated in a binder containing composition. Furthermore it is possible to apply the powder by co-extrusion of a mixture of a polymer and the powder. Moreover, the powder may be mixed with a polymer and applied by a dipping process.

In order to act with the biologically inhibiting effect the anode and cathode materials arranged on one or more surfaces on the inventive article must, of course, be electrically connected for the establishment of a galvanic couple in a body fluid acting as an electrolyte. According to the present invention this is ensured by the fact that the cathode and anode materials are in direct contact with each other. In this way the electrical resistance is kept at a minimum ensuring an optimal efficiency of the biological inhibition.

Further to the above mentioned cathode materials it is also possible to use graphite combined with silver as the anode provided the graphite and silver are in direct contact with each other. Such material differs from the material proposed in WO 99/46780 wherein graphite granules and silver granules are distributed separated from each other in a conductive base material. By the present invention the silver may be combined directly with the graphite granules in a way in which both the graphite and the silver will be exposed to the surroundings. This provides silver ion releasing granules which also maintain the ion releasing ability when distributed in a non-conducting but ion permeable material. An example of such combination is direct depositing of the silver on the graphite granules as an incomplete layer leaving openings exposing the graphite.

Accordingly the present invention also relates to an article to be inserted in a human or animal body cavity having a biologically inhibiting arrangement of electrically connected electrode materials on one or more surfaces of the article, which arrangement as electrode materials includes a anode material of Ag and a cathode material of graphite, which arrangement releases biological inhibiting ions of the Ag anode material or complexes of such ions when the biologically inhibiting arrangement is contacted with a body fluid, characterised in, that the cathode and anode materials are in direct contact with each other.

As mentioned above the combination Ag/graphite may in many cases be too efficient due to the high potential difference between Ag and graphite and the relatively good kinetically properties of graphite providing a high initial release of Ag ions. To obtain a sustained release over a prolonged period of time use of cathode materials having a potential closer to that of Ag are preferred.

Articles to be inserted in a body cavity such as catheters, gastroenteral or endotracheal tubes and drainage or suction systems give as mentioned above a high risk for infections. To avoid this, such articles can suitably be designed as an article according to the invention, which is an article of the mentioned type provided with the biologically inhibiting arrangement on those surfaces susceptible to microbiological contamination.

Important examples of articles to be inserted in a body cavity are intermittent urinary catheters and indwelling urinary catheters. Other examples are airway management products such as tracheal tubes (TT), endotracheal tubes (ET), suction catheters and gastroentrology tubes The invention also relates to other articles for use in contact with a body fluid susceptible for microbiological infections including articles for wound care, infusion devices, drainages and dialysis devices and similar devices.

An example of the indwelling urinary catheter is the conventional Foley catheter which is inserted into the bladder of an individual of either gender. This catheter extends upwardly through the urethra and the internal urethral orifice into the bladder. The end of the catheter includes an opening for drainage and an inflatable balloon to hold the opening in the bladder. As the indwelling catheter remains inserted for extended periods of time, for example up to one month, there is a very high risk for infections which risk can be controlled by the biologically inhibiting arrangement.

Accordingly an important embodiment of the inventive article is an intermittent or indwelling urinary catheter provided with the biologically inhibiting arrangement on those surfaces susceptible to microbiological contamination.

According to a preferred embodiment the biologically inhibiting arrangement is situated on the inner and/or outer surface of the article.

The present invention further relates to the use of the inventive article for the inhibition of microorganisms.

The inventive article is especially useful for the inhibition of microorganisms in a body fluid containing one or more compounds being able to decrease the potential of the metallic anode material by stabilisation of ions of the anode metal in the fluid. This stabilisation may be a complex binding of the free metal ions whereby the free ions are depleted from the surrounding electrolyte. The result is that the formation of ions of the anode metal is further supported which in other words means that the potential of the anode metal decreases.

As examples of this type of human or animal body fluids including urine or saliva containing fluids can be mentioned.

This type of body fluids contains ammonia (as $NH_4OH$) which binds ions of silver as a complex with the formula $Ag(NH_3)_2^+$. The change in potential appears from the standard reduction potentials E for the reactions (I) and (II):

$$Ag^+ + e^- = Ag \qquad (I)$$

$$Ag(NH_3)_2^+ + 2H_2O + e^- = Ag + 2\,NH_4OH \qquad (II)$$

$E = +0.800$ V versus SHE at 25° C.　　　　Reaction I:

$E = -0.551$ V versus SHE at 25° C.　　　　Reaction II:

Also other compounds included in an electrolyte may have an influence on the potential of silver. Thus following reactions are considered. The E values are relative to SHE at 25° C.:

$$Ag(S_2O_3)_2^{-3} + e^- = Ag + 2S_2O_3^{-2};\ E = +0.149\text{ V} \qquad \text{Reaction III:}$$

Thus thiosulfate is a complex binder for silver ions. According to Taylor et al. the compound $Ag(S_2O_3)_2^{-3}$ may be found on coral reefs (Taylor, M., A. Demayo and S. Reeder. 1980. Guidelines for Surface Water Quality. Vol. 1. Inorganic Chemical Substances. Silver. IWD, Water Quality Branch, Ottawa).

$$Ag(CN)_2^- + e^- = Ag + 2CN^-;\ E = -0.402\text{ V} \qquad \text{Reaction IV:}$$

Complex binder: cyanide ion, however cyanide is not relevant in biological systems.

$$Ag(CH_3COO)_2^- + e^- = Ag + 2CH_3COO^-;\ E = +0.759\text{ V}. \qquad \text{Reaction V:}$$

The acetate ion is a weak complex binder. $Ag(CH_3COO)_2^-$ is termed silver diacetate. It occurs in biological environments.

$$AgHS + e^- = Ag + HS^-;\ E = -0.113\text{ V} \qquad \text{Reaction VI:}$$

According to Taylor et al. AgHS, silver(I) hydrogen sulfide, may be of interest in for ex, ample the mouth of rivers (Taylor et al. cited above). Thus presence of $HS^-$ is contemplated in biological systems close to anaerobic conditions.

$$AgCl + e^- = Ag + Cl^-;\ E = +0.604\text{ V} \qquad \text{Reaction VII:}$$

$$NaAgCl_2 + e^- = Ag + NaCl + Cl^-;\ E = +0.393\text{ V} \qquad \text{Reaction VIII:}$$

Sodium dichloroargentate(I), $NaAgCl_2$, may according to Taylor et al. (cited above) be present in sea water. However, the equilibrium $$NaAgCl_2 = AgCl + Na^+ + Cl^- \qquad \text{Reactions VII+VIII:}$$

must be strongly displaced to the right as the equilibrium constant at 20° C. can be calculated to 2.968E+004.

It appears that ammonium ions are of interest as strong complex binders being present in biological systems including urine. In such systems also $HS^-$ may have influence. In presence of silver ions the sparingly soluble $Ag_2S$ may be formed. Silver can also form AgHS compounds which are soluble as unloaded ions. If the compound $Ag_2S$ first is formed it is very difficult to reduce.

$$Ag_2S + 2e^- = 2Ag + S^-;\ E = -0.655\text{ V}. \qquad \text{Reaction IX:}$$

The galvanic potentials of the anode material $p_A$ and the cathode material $p_c$ referred to in the present description and in the claims are—unless else is indicated—the actual potentials when contacted with the electrolyte in question. Thus as discussed above in case of a catheter when the electrolyte is urine the anode material may have a decreased potential relative to SHE even when the metallic anode material would have a positive potential in an electrolyte without complex binding ammonium ions.

The biological inhibiting effect of the inventive arrangement requires a sufficient difference $\Delta p$ between the respective potentials of the anode material $p_A$ and the cathode material $p_c$. Thus the value of $\Delta p = p_c - p_A$ should at least be 25 mV, preferably more than 45 mV and more preferred 50 mV or higher.

Typically the cathode material has a positive galvanic potential relative to SHE but depending of the value of $p_A$ even $p_c$ may be a negative value relative to SHE.

As mentioned above the rate with which the antimicrobial ions are driven into solution depends on the value of $\Delta p$. Thus for a given $p_A$ the release rate for the antimicrobial ions can be controlled by a suitable choice of a cathode material having a $p_c$ giving a low, medium or high value of $\Delta p$ to obtain a corresponding low, medium or high release rate. To this end the cathode material may be a single material or a combination of two ore more of the suggested electrically conductive non-metallic materials. The release rate may—as discussed above in the present specification—also depend on other factors.

BRIEF DESCRIPTION OF THE DRAWING

The invention is explained in detail below with reference to the drawing, in which FIG. 1 shows schematically a nutritional feeding tube to be inserted in the stomach, FIG. 2 shows schematically a partial longitudinal section of the feeding tube of FIG. 1 provided with the inventive arrangement on the inner and outer surfaces.

DESCRIPTION OF THE DRAWINGS

Figure 3:
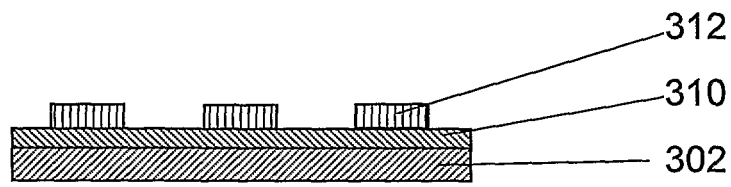
FIG. 3 shows schematically an embodiment of the inventive arrangement provided on a polymer substrate including a coating of anode material partially covered with sections of cathode material.

FIG. 1 shows an article according to the invention in the form of a conventional nutritional feeding tube comprising a longitudinal tube 2 having a front end 4 to be inserted into the stomach and a connection end 6. Adjacent to the front end 4 are a number of apertures 8 opening for the nutritional feed delivery from the tube 2 and supplied from the connection end 6.

A feeding tube of the type shown in FIG. 1 may typically have a length of about 14 to 100 cm and an outer diameter of the tube of about 1.3 to 4 mm.

According to the invention the inner and outer surfaces of the feeding tube 2 can be provided with a biological inhibiting arrangement as illustrated schematically in FIG. 2, which is a partial longitudinal section of the feeding tube 2 shown in FIG. 1. It should be noted that the dimensions shown in FIG. 2 are not correct as the sections of cathode material are enlarged in the figure to illustrate the principle.

According to FIG. 2 the feeding tube 2 is provided with the biological inhibiting arrangement on the inner surface with a layer of an anode material 10 which again is partially covered with a plurality of sections of a cathode material 12, which sections 12 are electrically connected to the layer of anode material 10. In the same way the biological inhibiting arrangement is also provided on the outer surface of the feeding tube 2 in the form of a layer of an anode material 14 which again is partially covered with a plurality of sections of a cathode material 16, which sections 16 are electrically connected to the layer of anode material 14. The size of the sections 12 and 16 calculated as the diameter on the surface can be between 1 nm and 10 µm, preferably between 10 nm and 1 µm. The distance between the sections 12 and 16 where the layers of anode material 10 and 14 will be exposed to the urine containing fluid acting as an electrolyte can similarly be between 1 nm and 10 µm, preferably between 10 nm and 1 µm.

The feeding tube shown in FIG. 1 is intended for relatively short time insertion into the stomach. In a preferred embodiment the biological inhibiting arrangement can also be provided on feeding tubes intended for a long term insertion as well as on an indwelling urinary catheter such as a conventional Foley catheter or another comparable catheter which typically remains in and inhabits the bladder and urethra for extended periods of time.

FIGS. 3-7 illustrated different embodiments of the biological inhibiting arrangement schematically.

FIG. 3 illustrates in general the embodiment also illustrated in FIG. 2. The biological inhibiting arrangement is provided on a non-conducting substrate 302. The substrate 302 can be of a non-conducting material such as a non-conductive polymeric material or ceramic or glass. The surface of the substrate 302 is coated or in another way covered with a layer of an anode material 310 which again is partially covered with a plurality of sections of a cathode material 312, which sections 312 are electrically connected to and in direct contact with the layer of anode material 310. The size of the sections 312 calculated as the diameter on the surface can be between 1 nm and 10 µm, preferably between 10 nm and 1 µm. The distance between the sections 312 where the layer of anode material 310 will be exposed to the electrolyte can similarly be between 1 nm and 10 µm, preferably between 10 nm and 1 µm.

An alternative embodiment of the biological inhibiting arrangement includes a construction similar to that shown in FIG. 3 but with the substrate covered with a layer of a cathode material which again is partially covered with sections of an anode material.

In stead of sections of the first electrode material any other structure partially covering the layer of the second electrode material is possible. An example is a net of the first material laid over the second material whereby the second material will be exposed to the electrolyte through the holes in the net.

By a conventional plating method it is known by the skilled person how to ensure a sufficiently continuous layer by the plating based on the plating conditions depending on different parameters such as plating time, plating temperature and other parameters. Based on this conventional knowledge it is also possible intentionally to select insufficient conditions such as a shorter plating time. In this way it is possible to make an insufficient layer of an electrode material as a structure only partially covering the other electrode material forming a biological inhibiting arrangement on an article according to the invention.

Figure 4:
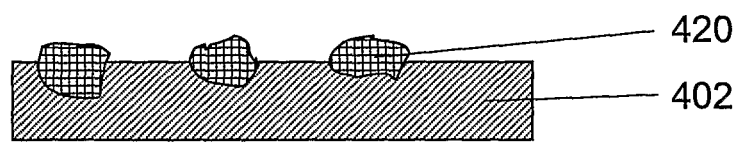
FIG. 4 shows schematically another embodiment with particles of the arrangement embedded partially in the surface of a non-conductive polymeric substrate.

In the embodiment illustrated in FIG. 4 the biological inhibiting arrangement is in the form of particles or flakes 420 containing both electrode materials. These particles or flakes 420 may be prepared by incorporation of smaller particles (for example grains or clusters) of the first electrode material into a matrix of the second electrode material or by aggregation or agglomeration of a mixture of smaller particles (grains) of the first and second electrode materials.

The particles or flakes 420 including both electrode materials may have a size between 1 and 40 µm or even more, whereas the size of the smaller particles or grains or clusters of a single electrode material calculated as the diameter can be between 1 nm and 10 µm, preferably between 10 nm and 1 µm.

The particles 420 are embedded partially in the surface of a substrate 402. This substrate 402 can be of a non-conducting material such as a polymeric material or ceramic or glass and may be a part of an inventive article to be inserted in a body cavity.

Figure 5:
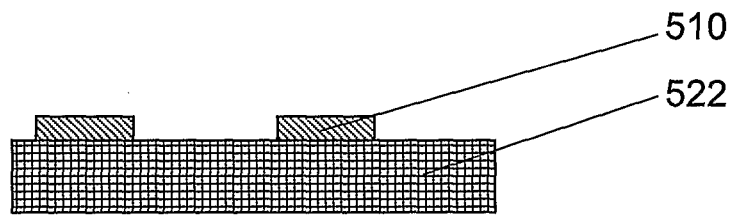
FIG. 5 shows schematically yet another embodiment including an electrical conductive polymer as a cathode material partially covered with sections of anode material.

In the embodiment illustrated in FIG. 5 the cathode material is an electrically conducting polymer 522 partially covered with sections 510 of anode material. The size of the sections 510 calculated as the diameter on the surface can be between 1 nm and 10 µm, preferably between 10 nm and 1 µm. The distance between the sections 510 where the electrical conductive polymeric cathode material 522 will be exposed to the electrolyte can similarly be between 1 nm and 10 µm, preferably between 10 nm and 1 µm. Again the partially covering anode material could also be provided as a net exposing the cathode material to the electrolyte through the holes in the net. Furthermore other incompletely covering layers of the anode material are contemplated.

Figure 6:
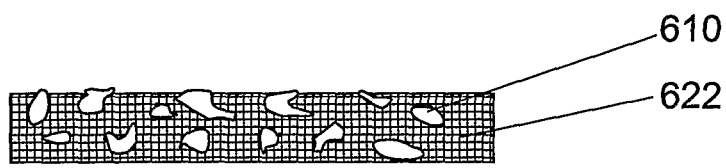
FIG. 6 shows schematically a still further embodiment including particles of anode material imbedded in a matrix of an electrical conductive polymer as cathode material.

It is also possible as illustrated in FIG. 6 to imbed particles 610 of anode material in a matrix 622 of an electrical conductive polymer as cathode material. The size of the particles 610 calculated as the greatest diameter can be between 1 nm and 10 µm, preferably between 10 nm and 1 µm. The distance between the particles 610 in the matrix 622 can similarly be between 1 nm and 10 µm, preferably between 10 nm and 1 µm.

Figure 7:
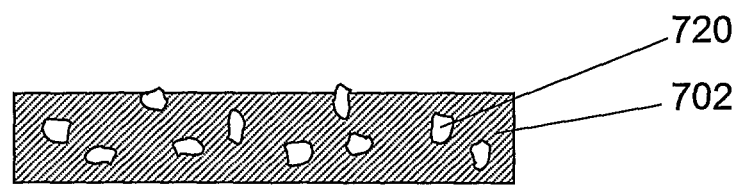
FIG. 7 shows schematically a still further embodiment including particles or flakes the inventive arrangement imbedded in a matrix of a non conducting material.

A further embodiment illustrated in FIG. 7 includes particles or flakes 720 similar to the particles or flakes 420 shown in FIG. 4 containing both electrode materials. The particles 720 are embedded in a substrate 702 of a non-conducting material wherein ions of the anode material will migrate out to the surface. Alternatively the particles or flakes 720 may be exposed to the surface by wear of the substrate 702. As an example this substrate 702 can be a coating of a polymeric material of the type having friction-reducing properties in wet condition conventionally used on catheters as disclosed in EP 586 324 and EP 591 091.

The particles or flakes 720 including both electrode materials may have a size between 10 nm and 40 µm, whereas the size of the smaller particles or grains or clusters of a single electrode material calculated as the diameter can be between 1 nm and 10 µm, preferably between 10 nm and 1 µm.

Figure 8:
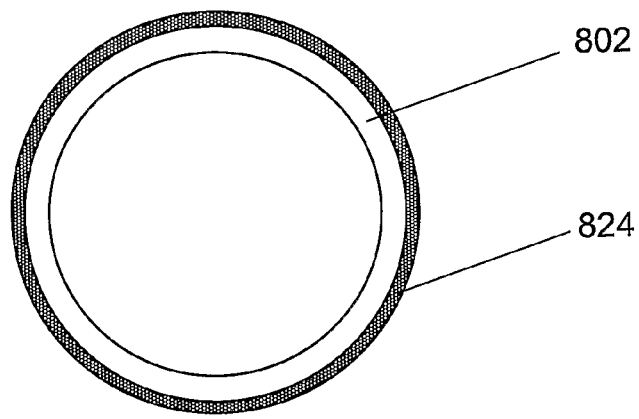
FIG. 8, shows a cross section of a tube of a first polymer with a coating of particles of a cathode material deposited with silver in a matrix of a second polymer on the outer surface of the tube.
Figure 9:
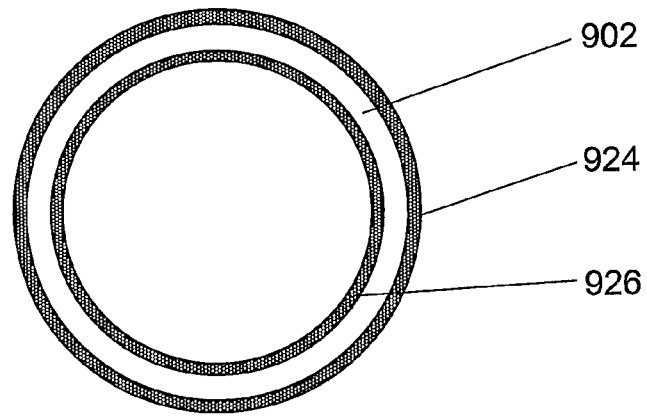
FIG. 9 shows a cross section of a tube of a first polymer with coatings of particles of a cathode material deposited with silver in a matrix of a second polymer on both the outer and the inner surfaces of the tube, FIG. 10 a, b and c show cross sections of a coextruded tube of a first polymer with a section of the tube wall formed by a matrix of a second polymer with particles of a cathode material deposited with silver.
Figure 10:
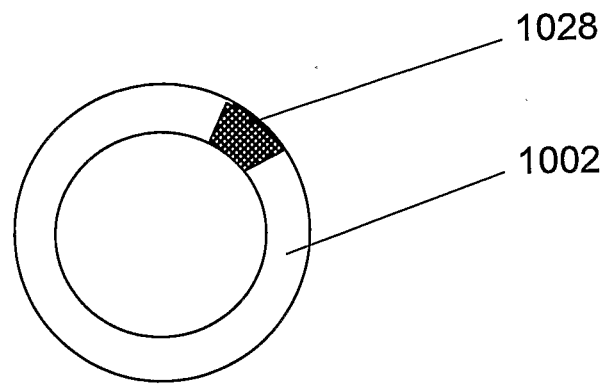
Figure 10:
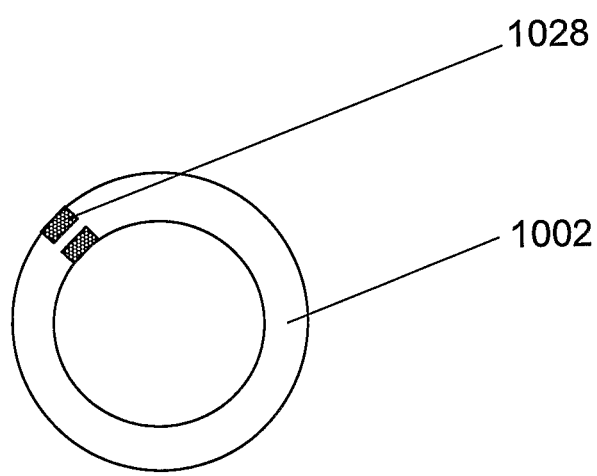
Figure 10:
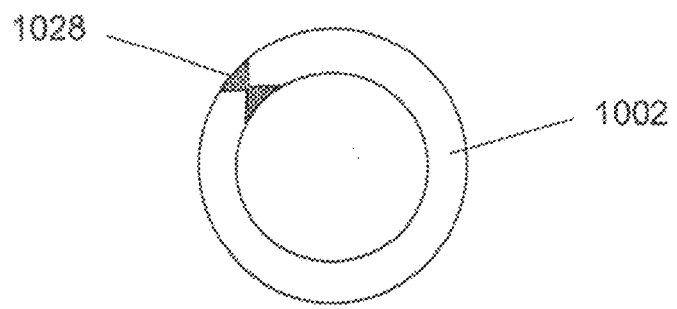

FIGS. 8, 9 and 10 show cross sections of tubes to be inserted in a body cavity prepared by co-extrusion of a first polymer 802, 902 and 1002 with a silver/cathode material in a matrix of a second polymer 824, 924, 926 and 1028. In the embodiment shown in FIG. 8 a tube 802 of the first polymer is provided with the biologically inhibiting arrangement exemplified with a powder of cathode material and silver in a matrix of the second polymer 824 as a layer on the outer surface of the tube. In a further embodiment shown in FIG. 9 a tube 902 of the first polymer is provided with the powder of cathode material and silver in a matrix of the second polymer as layers 924 and 926, respectively, both on the outer and on the inner surface of the tube.

In special embodiments shown in FIG. 10 a, b and c only a section 1028 of the tube cross section is provided with the biologically inhibiting powder whereas the remaining section 1002 is made of polymer without the powder. It is also possible to have more than one strand of the powder containing polymer. An advantage with this embodiment is that the flow in the tube can be inspected through the powder-free polymer which is transparent whereas the inhibiting section is provided at the full length of the tube and hence ensures biological inhibition along the entire tube.

Examples of the first and second polymers used in the above embodiments are PVC, PUR, silicone and other polymers acceptable for use in contact with the body. The first and second polymers may be of the same or different polymer types provided they are sufficient compatible to ensure that the materials will not delaminate.

Example 1

To estimate the actual potentials of some electrode materials in contact with urine as the electrolyte use was made of the following simulated standard urine solution for laboratory testing according to the European Standard EN 1616:1997 (Annex A.2.1):

|  | weight (g) |
| --- | --- |
| Urea | 25.0 |
| Sodium chloride | 9.0 |
| Disodium hydrogen orthophosphate, anhydrous | 2.5 |
| Ammonium chloride | 3.0 |
| Creatinine | 2.0 |
| Sodium sulfite, hydrated | 3.0 |
| Distilled water | q.s. to 1.0 liter |
| pH | approximately 6.6 |

Electrochemical Measurements

The electrochemical measurements were performed in a 400 ml electrochemical cell with a massive cylindrical working electrode with a length of 1 cm and a diameter of 1 cm. A cylindrical counter electrode of platinum was used, having a diameter of 6.5 cm and a length of 8 cm. A standard calomel electrode (SCE) was used as reference electrode.

Results:

Using 400 ml of the simulated standard urine solution at 37° C. following Open Corrosion Potentials (OCP) vs. Standard Hydrogen Electrode (SHE) for different materials as working electrodes were measured (table 1):

TABLE 1

| Material | Description | OCP after 10 min vs. SHE | OCP after 30 min vs. SHE | OCP after 60 min vs. SHE |
|---|---|---|---|---|
| Ag | Massive silver cylinder | 140 mV | 136 mV | 138 mV |
| Cu | Massive cobber cylinder | −49 mV | −74 mV | −90 mV |
| CrN | Physical vapour deposited chromium nitride on Stainless steel, AISI 304L | 367 mV | 341 mV | 328 mV |
| Graphite | Sprayed on AISI 304L | 215 mV | 186 mV | 198 mV |
| TiAlN | Physical vapour deposited titanium nitride on Stainless steel, AISI 304L | 223 mV | 172 mV | 89 mV |
| TiCN | Physical vapour deposited titanium carbon nitride on Stainless steel, AISI 304L | 210 mV | 172 mV | 89 mV |
| CrN-LT | Low temperature physical vapour deposited chromium nitride on Stainless steel, AISI 304L | 221 mV | 253 mV | 274 mV |
| (Ti,Cr)N | Physical vapour deposited (titanium, chromium) nitride on Stainless steel, AISI 304L | 255 mV | 231 mV | 211 mV |

The electrochemical properties of ceramics depend on the preparation process. Thus the above reported OPC values should not be considered at general properties of such materials.

Galvanic Coupling of Ag with Different Counter Electrodes

Table 2 shows the current density obtained by galvanic coupling of Ag with different cathode materials in a standard urine solution (EN 1616:1997) at 37° C.

TABLE 2

| Working electrode | Counter electrode | Description of counter electrode material | Current density after 10 min | Current density after 60 min | Current density after 120 min |
|---|---|---|---|---|---|
| Ag | Graphite | Sprayed on AISI 304L | 0.24 µA/cm$^2$ | 0.05 µA/cm$^2$ | 0.04 µA/cm$^2$ |
| Ag | TiN | Plasma Enhanced Chemical Vapour Deposition of titanium nitride on stainless steel, AISI 304L | 0.07 µA/cm$^2$ | 0.17 µA/cm$^2$ | 0.3 µA/cm$^2$ |
| Ag | CrN-LT | Low temperature physical vapour deposited chromium nitride on Stainless steel, AISI 304L | 0.209 µA/cm$^2$ | 0.073 µA/cm$^2$ | 0.035 µA/cm$^2$ |
| Ag | (Ti,Cr)N | Physical vapour deposited (titanium, chromium) nitride on Stainless steel, AISI 304L | 0.098 µA/cm$^2$ | 0.038 µA/cm$^2$ | 0.032 µA/cm$^2$ |
| Ag | TiAlN-nano | Physical vapour deposited nanocrystalline titanium nitride on Stainless steel, AISI 304L | 0.011 µA/cm$^2$ | 0.029 µA/cm$^2$ | 0.048 µA/cm$^2$ |

Similar to the results reported in table 1 the current densities reported in table 2 should not be considered at general properties of such ceramics since the electrochemical properties of ceramics depend on the preparation process.

Dissolution of Ag

Table 3 shows the dissolution rate of silver as calculated from the above galvanic coupling experiments, assuming 100% current yield

TABLE 3

| Working electrode | Counter electrode | Ag dissolution after 10 min | Ag dissolution after 60 min | Ag dissolution after 120 min |
|---|---|---|---|---|
| Ag | Graphite | 0.97 μg/(h × cm$^2$) | 0.2 μg/(h × cm$^2$) | 0.16 μg/(h × cm$^2$) |
| Ag | TiN | 0.28 μg/(h × cm$^2$) | 0.68 μg/(h × cm$^2$) | 1.2 μg/(h × cm$^2$) |
| Ag | CrN-LT | 0.84 μg/(h × cm$^2$) | 0.29 μg/(h × cm$^2$) | 0.14 μg/(h × cm$^2$) |
| Ag | (Ti,Cr)N | 0.39 μg/(h × cm$^2$) | 0.15 μg/(h × cm$^2$) | 0.13 μg/(h × cm$^2$) |
| Ag | TiAlN-nano | 0.04 μg/(h × cm$^2$) | 0.17 μg/(h × cm$^2$) | 0.19 μg/(h × cm$^2$) |

Conclusion:

The results demonstrate good possibilities of controlling the dissolution rate of Ag within a wide range in an urine media, for example by controlling the potential, which again is possible by choosing an appropriate cathode material and cathode/anode areas. Consequently it is possible to control of biological inhibition in the urine, because of the biological inhibiting effect of dissolved Ag.

The results further demonstrate that the expensive cathode materials of noble metals taught by DeLaurentis et al. (U.S. Pat. No. 5,295,979) can be replaced by a broad selection of less expensive electrically conductive non-metallic materials.

Example 2

The present example illustrates deposition of Ag on a fine powder of cathode material. Generally use of a very fine powder is advantageous in order to obtain a maximal surface area.

Types of Powders:

1: Graphite Powder from Merck:
Product name: Graphite fine powder extra pure. Catalogue No. 104206. Cas-No: 7782-42-5
2: Magnetite Powder from Sigma-Aldrich Denmark
Product name: Iron (II,III) oxide, powder, <5 micron, 98%.
Product number: 310069.
Cas-No: 1317-61-9

Figure 11:
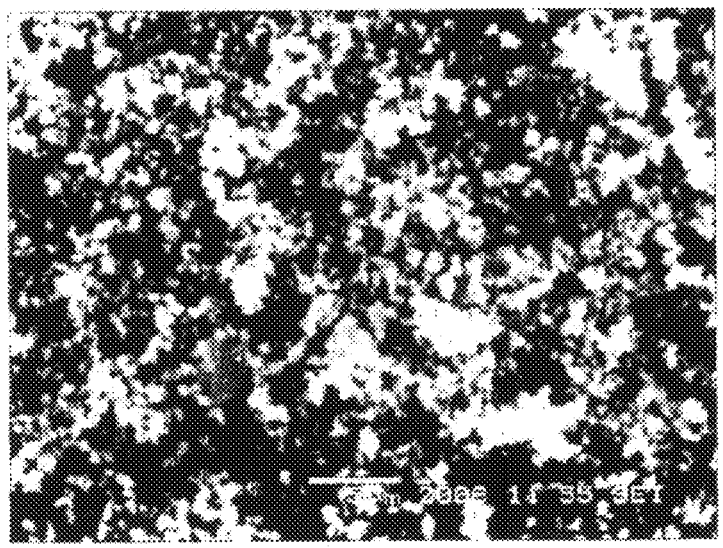
FIG. 11 is an image obtained by Scanning Electron Microscopy (SEM) of a graphite powder deposited with silver.

Deposition on $Fe_3O_4$ Powder:

$Fe_3O_4$ was dispersed in $H_2O$, with concentration of approximately 600 g/L. Glucose was dissolved in $H_2O$, with concentration of approximately 125 g/L, and subsequently added to the solution of dispersed $Fe_3O_4$ using a volume ratio of 2:3. Aqueous ammonia was added to a solution of 80 g/L $AgNO_3$, this solution was added to the powder/glucose solution using a volume ratio of 3:5 under continuously stirring in minimum 20 min. The powder was separated by filtration of the slurry, and washed with copious amounts of $H_2O$/ethanol. The powder was dried in an oven at approx. 70-90° C. FIG. 11 shows a Scanning Electron Microscopy (SEM) image of the obtained powder.

The present method for deposition of Ag on magnetite ($Fe_3O_4$) powder is in most cases also usable on other types of powders of cathode material. However, for certain materials it is advantageous to pre-treat the powder before the Ag deposition. An example of such pre-treatment is described below in case of graphite powder. It should be noted that further processes for chemical deposition of Ag are well known from the literature.

Deposition on Graphite Powder:

A solution of 50 g/L $SnCl_2$ and approximately 0.5 ml HCL was stirred and filtered. The graphite powder was dispersed into this solution with concentration of approximately 700 g/L. The graphite/$SnCl_2$ slurry was filtered and washed with copious amounts of water. The $SnCl_2$ treated graphite powder was dispersed in $H_2O$, with concentration of approximately 600 g/L. Glucose was dissolved in $H_2O$, with concentration of approximately 125 g/L, and subsequently added to the solution of dispersed graphite using a volume ratio of 2:3. Aqueous ammonia is added to a solution of 80 g/L $AgNO_3$, this solution was added to the powder/glucose solution using a volume ratio of 3:5 under continuously stirring in minimum 20 min. The powder was separated by filtration of the slurry, and wash with copious amounts of $H_2O$/ethanol. The powder was dried in an oven at approx. 70-90° C.

Figure 12:
FIG. 12 is an image obtained by Scanning Electron Microscopy (SEM) of a magnetite powder deposited with silver.

FIG. 12 shows a SEM image of the obtained powder.

Example 3

Figure 13:
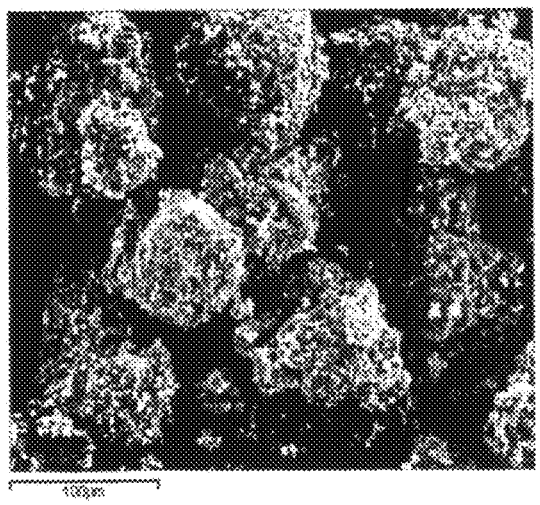
FIG. 13 is an image obtained by Scanning Electron Microscopy (SEM) of a tungsten carbide powder deposited with silver.

Particles of tungsten carbide (WC) with a particle size of 30-100 μm were deposited with Ag in a way similar to example 2. FIG. 13 shows a SEM image of the obtained powder. Analyses on different points on the surface confirm sufficiently irregular silver content throughout the surface.

Example 4

40% weight of the graphite powder coated with silver obtained in example 2 was mixed into commercial polyurethane (PUR) as the second polymer and coextruded with PVC as the first polymer into a tube with an outer diameter of 4 mm. The matrix of PUR with the silver coated graphite powder formed an outer layer on the inner PVC part of the obtained tube as shown in FIG. 8.

Example 5

60% weight of the magnetite powder coated with silver obtained in example 2 was mixed into commercial polyurethane (PUR) as the second polymer and coextruded with PVC as the first polymer into a tube with an outer diameter of 4 mm. The matrix of PUR with the silver coated magnetite powder formed an outer layer on the inner PVC part of the obtained tube as shown in FIG. 8.

Example 6

The present example describes Physical Vapour Deposition, PVD, of TiN and Ag on various polymer samples. Suitable polymer substrates include silicone, PVC, siliconised latex and silicone elastomer coated latex. The treatment of a substrate comprises Pre-treatment with $O_2$-plasma etch in 6 min, 630V and 0.32 A; $O_2$ flow=35 sccm;

Start pressure=2×10E-2 mbar

Ti sputtering at 0.8 kW in a $N_2$ atmosphere:

1: 2 min with Ar shutter, flow=330 sccm; Start pressure=3×10E-5; Sputter pressure=8×10E-3 mbar 2: 3 min without Ar shutter, flow=350 sccm 3: 15 min without Ar shutter, flow=350 sccm; $N_2$ flow=12 sccm; Sputter pressure=1.3×10E-2 mbar Ti sputtering is stopped and $N_2$ atmosphere removed by ventilation in approximately 5 sec.

Ag sputtering in 6 min at 0.8 kW, Ar flow 330 sccm.

It is also possible to deposit TiN and Ag on a metal substrate using PVD using suitably modified process parameters such as another pre-treatment known in the art.

Example 7

CFU Counting of Bacteria in Human Urine:

Microbiological inhibiting samples with surface areas of 7 mm×4 mm are placed into small containers under sterile conditions. 230 µl filtered human urine with bacteria culture of the concentration $10^5$-$10^6$ bacteria/ml at 37° C. are added to each container. Regularly samples of 1 µl of the solution are taken from the containers, and colony forming units, CFU, are counted.

Table 4 shows CFU counts of samples in human urine with addition of *Escherichia coli* bacteria. The TiN and Ag was deposited on a catheter as described in example 6

TABLE 4

| Time/minutes | CFU/µL for catheter PVD deposited with TiN/Ag | CFU/µL for pure silver |
|---|---|---|
| 0 | above 500 | above 500 |
| 30 | above 500 | above 500 |
| 60 | above 500 | above 500 |
| 90 | above 500 | above 500 |
| 120 | above 500 | above 500 |
| 150 | above 500 | above 500 |
| 180 | approx 400 | above 500 |
| 210 | approx 400 | above 500 |
| 240 | 270 | above 500 |
| 270 | 135 | above 500 |
| 300 | 60 | above 500 |
| 330 | 50 | above 500 |
| 360 | 55 | above 500 |
| 390 | 55 | above 500 |
| 420 | 30 | above 500 |

Table 5 shows CFU counts of samples in another batch of human urine, distinct from the human urine used in the example from table 4, with addition of *Escherichia coli* bacteria. The TiN and Ag was deposited on a catheter as described in example 6.

TABLE 5

| Time/minutes | CFU/µL for catheter PVD deposited with TiN/Ag | CFU/µL for pure silver |
|---|---|---|
| 0 | above 500 | above 500 |
| 30 | above 500 | above 500 |
| 60 | above 500 | above 500 |
| 90 | 180 | above 500 |
| 120 | 75 | above 500 |
| 150 | 95 | above 500 |
| 180 | 75 | above 500 |
| 210 | 70 | above 500 |
| 240 | 30 | above 500 |
| 270 | 10 | above 500 |
| 300 | 5 | above 500 |
| 330 | 0 | above 500 |
| 360 | 0 | above 500 |
| 390 | 30 | above 500 |
| 420 | 15 | above 500 |

In the above example 7 the effect from the silver dissolution by the galvanic coupling of the PVD deposited cathode is convincing. In this case the TiN is deposited by using a reactive PVD process followed by sputtering of silver (anodic material) on the top of the coating.

Typically a treatment with titanium on a polymer surface will cause the formation of TiC, by a chemical reaction with the polymer, and a treatment later with nitrogen will probably cause the formation of TiCN and/or a mixture of TiN or TiC. All the mentioned material will typically show a potential 80-100 mV more positive than silver according to table 1.

The above description of the invention reveals that it is obvious that it can be varied in many ways. Such variations are not to be considered a deviation from the scope of the invention, and all such modifications which are obvious to persons skilled in the art are also to be considered comprised by the scope of the succeeding claims.

The invention claimed is:

1. The article to be inserted in a human or animal body cavity having a biologically inhibiting arrangement of electrically connected electrode materials present on one or more surfaces of the article as added electrode materials other than the material of the article itself, which arrangement as electrode materials includes at least one or a plurality of metallic anode materials and an electrically conductive nonmetallic cathode materials in direct contact with each other so that when the article is inserted in the body it forms a galvanic couple in the presence of an electrolyte, wherein the arrangement of electrode materials is configured to provide a potential of the cathode material that is higher than the potential of the anode material and a value of the difference Δp between the respective potentials of the anode material ($p_A$) and the cathode material ($p_C$) that is at least 25 mV, so that the arrangement has an in vivo action which releases biological inhibiting ions of the metallic anode material or complexes of such ions when the biologically inhibiting arrangement is contacted with an electrolyte comprising a body fluid, wherein said conductive nonmetallic cathode material is selected from the group consisting of graphite, nitrides, borides, carbides, mixed nitrides, silicides, oxides having a spinel structure of the formula $XY_2O_4$ wherein X is divalent Mg, Zn, Fe or Mn and Y is trivalent Al, Fe, Mn or Cr, conductive polymers and combinations of two or more thereof.

2. The article according to claim 1, wherein the cathode material includes a material selected among nitrides of Fe, Ga, Cr, Ti; mixed nitrides including TiAlN and TiCN; borides of Mg, Ti, Nb, Mo, Zr, Cr, Ca, Ta, W and Fe; carbides of Si, Mo, Nb, Ta, Ti, Fe, V, B and W, magnetite, chromite, conductive polymers including polyaniline, polypyrole, polythiophene, polyacetylene, polythiophene, poly[3,4-dialkoxythiophene], poly[3,4-ethylenedioxythiophene] and poly[3,4-ethylenedioxythiophene]poly-(styrenesulfonate) and combinations of two or more thereof.

3. The article according to claim 1, wherein the cathode material is doped in order to improve the conductivity.

4. The article according to claim 1, wherein the arrangements in two or more areas on the surface of the article have different release rates of biological inhibiting ions.

5. The article according to claim 1, wherein the metallic anode material is selected from the group consisting of Zn, Ag, Cu and a combination of two or three thereof.

6. The article according to claim 5, wherein the metallic anode material is Ag.

7. The article according to claim 1, wherein at least one of the electrode materials is distributed as a plurality of sections electrically connected to the other electrode material.

8. The article according claim 1 including a layer of one of the electrode materials covered with an incomplete layer of the other electrode material.

9. The article according to claim 1 including immobilized particles or flakes of one of the electrode materials contaminated with the other electrode material.

10. The article according to claim 1, wherein the biologically inhibiting arrangement comprises a pattern of electrically connected layers of the anode material and the cathode material applied on separated surface areas.

11. The article according to claim 1, wherein one or more biologically inhibiting arrangements of anode/cathode combinations are provided with a controlled pattern of release rates of biologically inhibiting ions over time and/or at different surface locations on the article.

12. The article according to claim 1, wherein the anode material and/or the cathode material have been applied by a plating method.

13. The article according to claim 12, wherein the plating method is electroless plating, electrochemical plating, a physical vapour deposition process (PVD-process), a chemical vapour deposition process (CVD-process), thermal spraying or a combination of two or more of these processes.

14. The article according to claim 1, wherein the anode material and/or the cathode material have been applied on one or more surfaces of the article as a powder.

15. The article according to claim 14, wherein the powder has been applied by a painting or printing method incorporated in a binder containing composition.

16. The article according to claim 14, wherein the powder has been applied by co-extrusion of a mixture of a polymer and the powder.

17. The article according to claim 14, wherein the powder has been mixed with a polymer and applied by a dipping process.

18. The article according to claim 1, wherein it is an article to be inserted in a body cavity such as a catheter, a gastroenteral or endotracheal tube, or a part of a drainage or suction device.

19. The article according to claim 18, wherein the arrangement is situated on the inner and/or outer surface of the article.

20. The article according to claim 18, wherein the article is an intermittent or indwelling urinary catheter.

21. The article to be inserted in a human or animal body cavity having a biologically inhibiting arrangement of electrically connected electrode materials present on one or more surfaces of the article as added electrode materials other than the material of the article itself, which arrangement as electrode materials includes an anode material of Ag and a cathode material of graphite in direct contact with each other so that when the article is inserted in the body it forms a galvanic couple in the presence of an electrolyte, wherein the arrangement of electrode materials is configured to provide a potential of the cathode material that is higher than the potential of the anode material and a value difference ($\Delta p$) between the respective potentials of the anode material ($p_A$) and the cathode material ($p_c$) that is at least 25 mV, so that the arrangement has an in vivo action which releases biological inhibiting ions of the Ag anode material or complexes of such ions when the biologically inhibiting arrangement is contacted with an electrolyte comprising a body fluid.

22. An article to be inserted in a human or animal body cavity having a biologically inhibiting arrangement of electrically connected electrode materials present on one or more surfaces of the article as added electrode materials other than the material of the article itself, which arrangement as electrode materials includes one or a plurality of metallic anode materials and electrically conductive nonmetallic cathode materials, wherein the anode and cathode materials are in direct contact with each other so that when the article is inserted in the body it forms a galvanic couple in the presence of an electrolyte, with the anode and cathode materials having diameter sizes of between 1 nm and 10 μm, wherein the arrangement of electrode materials is configured to provide a potential of the cathode material that is higher than the potential of the anode material and a value of the difference $\Delta p$ between the respective potentials of the anode material ($p_A$) and the cathode material ($p_c$) that is at least 25 mV, so that the arrangement has an in vivo action which releases biological inhibiting ions of the metallic anode material or complexes of such ions when the biologically inhibiting arrangement is contacted with an electrolyte comprising a body fluid, wherein said conductive nonmetallic cathode material is selected from the group consisting of nitrides, borides, graphite, carbides, mixed nitrides, silicides, oxides having a spinel structure of the formula $XY_2O_4$ wherein X is divalent Mg, Zn, Fe or Mn and Y is trivalent Al, Fe, Mn or Cr, conductive polymers and combinations of two or more thereof.

23. The article according to claim 22 wherein the conductive nonmetallic cathode material is selected from the group consisting of graphite, silicides, oxides having a spinel structure, conductive polymers and combinations of two or more thereof, wherein the conductive polymers include polyaniline, polypyrole, polythiophene, polyacetylene, polythiophene, poly[3,4-dialkoxythiophene], poly[3,4-ethylenedioxythiophene] and poly[3,4-ethylenedioxythiophene] poly-(styrenesulfonate) and the oxides having a spinel structure have the formula $XY_2O_4$ wherein X is divalent Fe or Mg and Y is trivalent Al, Fe, Mn or Cr.

24. The article according to claim 22, wherein the metallic anode material is selected from the group consisting of Zn, Ag, Cu and a combination of two or three thereof.

* * * * *